United States Patent
Arndt et al.

(10) Patent No.: US 11,596,952 B2
(45) Date of Patent: Mar. 7, 2023

(54) ESTERQUATS FOR THE FLOTATION OF NON-SULFIDIC MINERALS AND ORES, AND METHOD

(71) Applicant: Clariant International Ltd., Muttenz (CH)

(72) Inventors: Matthias Arndt, Mannheim (DE); Klaus-Ulrich Pedain, Dietzenbach-Steinberg (DE); Pia Mueller, Efringen-Kirchen (DE); Gemma Solduga Ramirez, Mannheim (DE); Yves Schunk, Frankfurt (DE); Jozef Kochan, Hofheim am Taunus (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

(21) Appl. No.: 16/962,411

(22) PCT Filed: Jan. 16, 2018

(86) PCT No.: PCT/EP2018/050914
§ 371 (c)(1),
(2) Date: Jul. 15, 2020

(87) PCT Pub. No.: WO2019/141343
PCT Pub. Date: Jul. 25, 2019

(65) Prior Publication Data
US 2020/0360938 A1    Nov. 19, 2020

(51) Int. Cl.
*B03D 1/01* (2006.01)
*B03D 1/02* (2006.01)
(Continued)

(52) U.S. Cl.
CPC ............... *B03D 1/011* (2013.01); *B03D 1/01* (2013.01); *B03D 1/02* (2013.01); *C07C 213/08* (2013.01);
(Continued)

(58) Field of Classification Search
CPC ...... B03D 1/011; B03D 1/02; B03D 2201/02; B03D 2203/04; C07C 213/06; C07C 213/08; C07C 219/08
(Continued)

(56) References Cited

U.S. PATENT DOCUMENTS 2,173,448 A * 9/1939 Epstein ................ B01F 17/00
554/25
4,474,619 A * 10/1984 Meyer ...................... B03D 1/01
209/166

(Continued)

FOREIGN PATENT DOCUMENTS

| AU | 708335 | 8/1999 |
|---|---|---|
| CL | 1999001065 | 11/1999 |

(Continued)

OTHER PUBLICATIONS

C. L. Noller, "Polycarbonsäuren", Lehrbuch der Organischen Chemie, Berlin, Heidelberg, (19600101), URL: https://www.springer.com/de/book/9783642873256, (May 22, 2018), XP055477296, 6 pages.
(Continued)

*Primary Examiner* — Peter Keyworth
(74) *Attorney, Agent, or Firm* — Tod A. Waldrop (57) ABSTRACT

The invention relates to esterquats which can be obtained by reacting di- or trialkanolamines with a mixture of fatty acids and polycarboxylic acids, and the esters obtained in this manner are then quaternized with an alkylating agent, wherein the di- or trialkanolamines correspond to formula (I), (Continued)

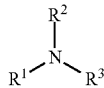

(I)

in which R1 and R2 independently of one another represent hydroxyalkyl groups with 1 to 20 carbon atoms, hydroxyalkenyl groups with 2 to 20 carbon atoms and 1, 2, or 3 double bonds, or addition products of 1 to 20 mol ethylene oxide on a hydroxyethyl group and R3 represents hydrogen, an alkyl group with 1 to 20 carbon atoms, an alkenyl group with 2 to 20 carbon atoms and 1, 2, or 3 double bonds, a hydroxyalkyl group with 1 to 20 carbon atoms, a hydroxyalkenyl group with 2 to 20 carbon atoms and 1, 2, or 3 double bonds, or addition products of 1 to 20 mol ethylene oxide on a hydroxyethyl group; the fatty acids correspond to formula (II),

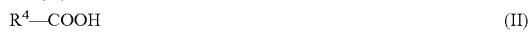

(II)

in which R4 represents an aliphatic, linear, or branched hydrocarbon group with 5 to 29 carbon atoms and 0, 1, 2, or 3 double bonds; and the polycarboxylic acids correspond to formula (III),

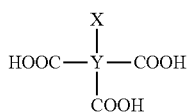

(III)

in which Y represents a carbon atom or a saturated or unsaturated aliphatic hydrocarbon group with 2 to 5 carbon atoms, said group optionally having one or more hydroxyl groups, and X represents hydrogen or a hydroxy- or carboxylic acid group. The invention also relates to the use of said esterquats as collectors for the flotation of non-sulfidic minerals.

18 Claims, 1 Drawing Sheet

(51) Int. Cl.
  *C07C 213/08* (2006.01)
  *C07C 219/08* (2006.01)

(52) U.S. Cl.
  CPC ...... *B03D 2201/02* (2013.01); *B03D 2203/04* (2013.01); *C07C 219/08* (2013.01)

(58) Field of Classification Search
  USPC .......................................... 209/166; 252/61
  See application file for complete search history.

(56) References Cited

U.S. PATENT DOCUMENTS

| | | | | |
|---|---|---|---|---|
| 4,732,669 | A * | 3/1988 | Nimerick | B03D 1/01 |
| | | | | 209/166 |
| 6,145,667 | A | 11/2000 | Rothenberg | |
| 8,936,159 | B2 * | 1/2015 | Gorochovceva | B03D 1/02 |
| | | | | 209/166 |
| 9,027,757 | B2 | 5/2015 | Pedain | |
| 10,100,146 | B2 * | 10/2018 | Smolko-Schvarzmayr | |
| | | | | B03D 1/011 |
| 2013/0092603 | A1 | 4/2013 | Nagaraj | |
| 2015/0021274 | A1 * | 1/2015 | Arts | C08G 63/6854 |
| | | | | 210/735 |
| 2019/0046994 | A1 * | 2/2019 | Jorda | B03D 1/011 |

FOREIGN PATENT DOCUMENTS

| | | |
|---|---|---|
| CL | 2011001023 | 11/2011 |
| CL | 2014000985 | 8/2014 |
| DE | 64275 | 10/1968 |
| DE | 2547987 | 4/1977 |
| DE | 4026184 | 2/1992 |
| DE | 4308792 | 4/1994 |
| DE | 4409322 | 4/1995 |
| DE | 49602856 | 7/1997 |
| DE | 102008056338 | 5/2010 |
| EP | 1949963 | 7/2008 |
| EP | 1949964 | 7/2008 |
| WO | 9101295 | 2/1991 |
| WO | WO 2008089906 A1 * | 7/2008 |

OTHER PUBLICATIONS

H. Schubert, Aufbereitung fester mineralischer Rohstoffe, 2.. Auflage, Leipizig 1977, S. 310-311.
International Search Report for PCT/EP2018/050914, dated Jun. 6, 2018, 2 pages.
R. Houot, "Beneficiation of phosphatic ores through flotation: review of industrial applications and potential developments", International Journal of Mineral Processing, 9, 1982, 353-384.

* cited by examiner

Figure 1

ESTERQUATS FOR THE FLOTATION OF NON-SULFIDIC MINERALS AND ORES, AND METHOD

The present invention relates to new esterquats obtainable by reading di- or trialkanolamines with fatty acids and polycarboxylic acids and quaternizing the resultant esters, optionally after alkoxylation. The invention further pertains to a method for froth flotation of non-sulfidic minerals and ores, and more particularly to the use of the esterquats as collectors in a froth flotation method.

Flotation is a separating technology commonly used in the processing of minerals. It sees the crude ores separated into valuable material and gangue. Non-sulfidic minerals and ores in the context of the present invention include, for example, calcite, apatite, fluorite, scheelite, baryte, iron oxides, and other metal oxides, examples being the oxides of titanium and zirconium, and also certain silicates and aluminosilicates.

With flotation-based processing operations, the mineral or ore is first comminuted by dry or preferably wet grinding and is suspended in water. Then the collector, frequently in conjunction with frothers and other auxiliary reagents, such as depressants or activators, is added to the ore/water mixture in order to separate the valuable material from the unwanted gangue of the ore. After a certain time for the reagents to act (conditioning), air is introduced into the suspension, and is finely distributed by virtue of the cell geometry, and generates a froth at the surface of the flotation cell.

The collector hydrophobizes the surface of the minerals, so that they attach to the bubbles of air when air bubble and particle meet. The hydrophobizing of the minerals by the collectors is selective, so that in the case of direct flotation the variable minerals float to the surface and in the case of reverse flotation the gangue particles collect at the surface. The froth containing solids is stripped off at the cell surface and transported on. The aim of flotation is to maximize the yield in the separation of the gangue from the valuable material of the minerals and ores, the intention being at the same time to achieve a high level of enrichment of the valuable mineral.

In the case of non-sulfidic flotation, as in the reverse flotation of calcite, for example, the collectors used comprise, in particular, anionic, cationic, and ampholytic surfactants, which usually also have a frothing effect, so removing the need for further addition of a frother. Calcite is an important filler in the paper industry, allowing the whiteness and the transparency of the paper to be set. Calcite minerals, however, are often accompanied by silicates, iron oxides, etc., which have a negative influence on the purity and must therefore be removed.

WO-2008/089906 is regarded as prior art, and describes the particular effectiveness of using polymeric esterquats as collectors for silicates and magnesium salts in non-sulfidic flotation.

DE-102008056338 teaches the use of a composition of

A) at least one quaternary ammonium compound which contains at least one organic radical which has 1 to 36 carbon atoms, is bonded to the ammonium nitrogen atom, and optionally comprises heteroatoms, and B) at least one amine alkoxylate ester of the formula (1) or a salt thereof in which
A and B independently of one another are a $C_2$ to $C_5$ alkylene radical
$R^1$ is a $C_8$ to $C_{24}$ alkyl radical or alkenyl radical
$R^2$, $R^3$, and $R^4$ independently of one another are H or a $C_8$ to $C_{24}$ acyl radical, with the proviso that at least one of the radicals $R^2$, $R^3$, or $R^4$, is a $C_8$ to $C_{24}$ acyl radical
x, y, and z independently of one another are an integer from 0 to 50, with the proviso that x+y+z is an integer from 1 to 100,
in amounts of 10 to 5000 g/ton of ore, as a collector in silicate flotation.

The object of the present invention is to provide an improved collector for various flotation processes that allows a better selectivity to be achieved for a given amount of collector and with the same high yield. The collector ought in particular to be suitable for reverse calcite flotation, and to yield a purer calcite while minimizing loss.

Surprisingly it has been found that esterquats that are obtained by reacting di- or trialkanolamines with fatty acids and polycarboxylic acids and subjecting the resultant esters—optionally after alkoxylation—to conventional quaternization constitute improved collectors for various flotation processes. Particularly in the context of reverse calcite flotation, the new esterquats have proven surprisingly to be even more effective, and additionally they have very good biodegradability, which is important particularly to the producers of calcite.

A subject of the present invention, therefore, are esterquats obtainable by reacting di- or trialkanolamines with a mixture of fatty acids and polycarboxylic acids and quaternizing the resultant esters subsequently with an alkylating agent, where the di- or trialkanolamines conform to the formula (I)

in which
$R^1$ and $R^2$ independently of one another are hydroxyalkyl radicals having 1 to 20 carbon atoms, hydroxyalkenyl radicals having 2 to 20 carbon atoms and 1, 2, or 3 double bonds, or adducts of 1 to 20 and preferably 2 to 5 mol of ethylene oxide onto a hydroxyethyl radical, and
$R^3$ is hydrogen, an alkyl radical having 1 to 20 carbon atoms, an alkenyl radical having 2 to 20 carbon atoms and 1, 2, or 3 double bonds, a hydroxyalkyl radical having 1 to 20 carbon atoms, a hydroxyalkenyl radical having 2 to 20 carbon atoms and 1, 2, or 3 double bonds, or adducts of 1 to 20 and preferably 2 to 5 mol of ethylene oxide onto a hydroxyethyl radical, and where the fatty acids conform to the formula (II), $$R^4—COOH \quad (II)$$

in which
R$^4$ is an aliphatic, linear or branched hydrocarbon radical having 5 to 29 carbon atoms and 0, 1, 2, or 3 double bonds, and where
the polycarboxylic acids conform to the formula (III)

(III)

in which
Y is a carbon atom or a saturated or unsaturated, aliphatic hydrocarbon group having 2 to 5 carbon atoms and optionally carrying one or more hydroxyl groups, and
X is hydrogen, a hydroxyl or a carboxylic acid group.

A further subject of the present invention relates to the use of the esterquats of the invention as collectors in the flotation of non-sulfidic minerals or ores.

A further subject of the present invention relates to a method for flotation of non-sulfidic minerals or ores, wherein the esterquat of the invention is added as a collector.

A further subject of the invention relates to a method for producing esterquats, where di- or trialkanolamines are reacted with a mixture of fatty acids and polycarboxylic acids and the resulting esters are optionally alkoxylated and then quaternized in a known way.

In the flotation method, the crude ore is first ground and then is mixed with water to form a suspension. The collector of the invention and, as and when required, further reagents are added to this mixture, and air is blown in, causing a layer of froth to form, in which the hydrophobic mineral particles have floated.

Surprisingly it has been observed that the new esterquats are exceptionally effective collectors for the flotation of non-sulfidic minerals and ores, especially with regard to the presence of silicates and/or magnesium salts in the minerals or ores. The collectors according to the present invention are more effective in comparison to the conventional esterquats with monocarboxylic and polycarboxylic acids, while having a very high degree of biodegradability. The products in particular have proven very useful for the separation of silicatic minerals from calcite by froth flotation.

Esterification with a mixture of fatty acids and polycarboxylic acids provides new esterquats of the formula (1), which surprisingly are distinguished from products of the prior art not only in particularly good environment compatibility, but also in outstanding flotation yields.

Radicals R$^1$ and R$^2$ in the di- or trialkanolamines of the formula (I), independently of one another, are preferably hydroxyalkyl radicals having 2 to 5 carbon atoms, or hydroxyalkenyl radicals having 2 to 5 carbon atoms and 1, 2, or 3 double bonds, or adducts of 2 to 5 mol of ethylene oxide onto a hydroxyethyl radical.

R$^3$ preferably represents alkyl radicals having 1 to 20 carbon atoms, alkenyl radicals having 2 to 20 carbon atoms, hydroxyalkyl radicals having 2 to 5 carbon atoms, or hydroxyalkenyl radicals having 2 to 5 carbon atoms and 1, 2, or 3 double bonds.

Preferred di- or trialkanolamines of the formula (I) are methyldiethanolamine (MDA), diethanolamine (DEA), diethoxylated oleylamines, and triethanolamine (TEA).

One particularly preferred embodiment of the present invention uses triethanolamine.

In the fatty acids of the formula (II), R$^4$ is preferably an aliphatic, linear or branched radical having 7 to 21 carbon atoms and 0, 1, 2, or 3 double bonds.

Preferred fatty acids are aliphatic carboxylic acids selected from the group consisting of caprylic acid, capric acid, lauric acid, undecylenic acid, isotridecanoic acid, myristic acid, myristoleic acid, palmitic acid, palmitoleic acid, stearic acid, isostearic acid, oleic acid, petroselinic acid, elaidic acid, petroselinic acid, linoleic acid, linolenic acid, eleostearic acid, arachidic acid, gadoleic acid, behenic acid, erucic acid, and cetoleic acid, and also technical mixtures thereof. These carboxylic acids are formed, for example, in the pressure cleavage of natural fats and oils, in the reduction of aldehydes from the Roelen oxosynthesis or the dimerization of unsaturated fatty acids. The stated fatty acids, if unsaturated, may be used in their hydrogenated or partly hydrogenated form.

Likewise preferred are technical fatty acid mixtures comprising fatty acids having 12 to 18 carbon atoms, examples being coconut oil, palm oil, palm kernel oil or tallow fatty acids.

The polycarboxylic acid of the formula (III) comprises preferably as radical Y a saturated or unsaturated aliphatic hydrocarbon group having 3 or 4 carbon atoms, it being possible for said group optionally to carry one or more hydroxyl groups.

Preferred polycarboxylic acids are propane-1,2,3-tricarboxylic acid, aconitic acid, isocitric acid, and, in particular, citric acid.

The fatty acids and the polycarboxylic acids can be used preferably in a molar ratio of fatty acid to polycarboxylic acid=1:10 to 10:1. It has proven particularly advantageous to set a molar ratio of 1:1 to 8:1.

The di- or trialkanolamines on the one hand and acids—that is, fatty acids and polycarboxylic acids together—on the other hand, may be used preferably in a molar ratio of di- or trialkanolamines to acids of 1:0.25 to 1:3.0, more particularly in a molar ratio of 1:0.6 to 1:1.5.

The esterification can be carried out in a conventional way, as described in WO 91/01295, for example. In one advantageous embodiment the reaction is carried out at temperatures between 120° C. and 220° C. and more particularly from 140° C. to 200° C. and pressures of 0.01 to 1 bar. A catalyst can be used to accelerate the esterification reaction. Suitable catalysts are acids, preferably hypophosphorous and phosphorous acids and their alkali metal salts, preferably sodium hypophosphite, which can be used in amounts of 0.001 to 0.5 weight %, and preferably in amounts of 0.005 to 0.15 weight %, based on the starting materials.

For the esterification it is possible to use mixtures of the fatty acids and polycarboxylic acids, or else to conduct the esterification with the two components one after another.

With regard to particularly high color quality and color stability, the accompanying use of borohydrides of alkali metals and/or alkaline earth metals, such as potassium, magnesium, and especially sodium borohydride, for example, has proven advantageous in the esterification. These compounds are customarily employed in amounts of 50 to 1000 ppm and especially 100 to 500 ppm—again based on the starting materials—as described in the application DE-C1-44 09 322.

Treatment of the ester with peroxide compounds, or a mixture of peroxide compounds and alkali metal boranates, prior to the quaternization also leads to high color quality and color stability. Peroxide compounds contemplated, besides percarboxylic acids and percarbonates, are preferably hydrogen peroxide. Alkali metal boranates comprehend lithium, potassium, and, preferably, sodium boranates. Advantageously the peroxide compounds and the alkali metal boranates are each used in amounts of 0.005 to 0.1%, preferably 0.03 to 0.06%, by weight based on the esterification products, as described in DE 43 08 792.

For the production of polyalkylene oxide-containing esterquats there are two possible alternative procedures. Firstly, ethoxylated alkanolamines can be used. The advantage of this is that the alkylene oxide distribution in the subsequent esterquat in relation to the OH groups of the amine is approximately equal. A disadvantage, however, is that the esterification becomes more difficult on steric grounds. The preferred technique, therefore, is to alkoxylate the ester before the quaternization. This can be done in a conventional way, i.e., in the presence of basic catalysts and at elevated temperatures. The catalyst contemplated comprises, for example, alkali metal and alkaline earth metal hydroxides and alkoxides, preferably sodium hydroxide and more particularly sodium methoxide. The amount for use is customarily 0.5% by 5% and preferably 1% to 3% by weight, based on the starting materials. Free hydroxyl groups are alkoxylated primarily when using these catalysts.

Where, however, the catalysts used comprise calcined hydrotalcites or hydrotalcites hydrophobized with fatty acid, there is also insertion of the alkylene oxides into the ester bonds. This technique is preferred when the desire is for an alkylene oxide distribution which comes close to that obtained from using alkoxylated di- or trialkanolamines. Alkylene oxides used may be ethylene oxide and propylene oxide and also mixtures thereof (random or block distribution). The reaction is carried out customarily at temperatures in the range from 100 to 180° C. The incorporation of an average of 1 to 10 mol of alkylene oxide per mole of ester raises the hydrophilicity of the esterquats, improves the solubility, and reduces the reactivity with respect to anionic surfactants.

The quaternization of the esters may be carried out in a conventional way. Although the reaction with the alkylating agents can also be carried out in the absence of solvents, it is advisable to also use at least small amounts of water or short-chain alcohols, preferably isopropyl alcohol, to produce concentrates which have a solids fraction of at least 40% and more particularly at least 60% by weight. The term "short-chain alcohols" in this invention denotes a C chain length of $C_1$-$C_{10}$.

Suitable alkylating agents include alkyl halides such as methyl chloride, dialkyl sulfates such as dimethyl sulfate or diethyl sulfate, or dialkyl carbonates such as dimethyl carbonate or diethyl carbonate, for example. The alkylation is preferably a methylation or an ethylation, more particularly a methylation.

The esters and the alkylating agents are customarily used at near stoichiometry in a molar ratio—based on the nitrogen content of the ester—of 1:0.50 to 1:1.05, preferably 1:0.90 to 1:0.98. The reaction temperature is commonly 40 to 110° C. and more particularly 50 to 80° C. Following the reaction, it is advisable to destroy unreacted alkylating agent by addition, for example, of ammonia, an alkanolamine, an amino acid, or an oligopeptide, as is described for example in DE-A1 40 26 184.

In certain cases it may be of advantage to modify, adapt or even support the properties of the esterquats through the addition of defined co-collectors, such as cationic or amphoteric surfactants, for example.

Cationic surfactants which can be used as co-collectors are to be selected in particular from the following:
primary aliphatic amines
alkylenediamines with alpha-branched alkyl radicals
hydroxyalkyl-substituted alkylenediamines
water-soluble acid addition salts of these amines
quaternary ammonium compounds, especially
quaternized N,N-dialkylaminoalkylamines.

Suitable primary aliphatic amines are, in particular, $C_8$-$C_{22}$ fatty acids of fatty acids from natural fats and oils. Typical examples are n-octylamine, n-decylamine, n-dodecylamine, n-tetradecylamine, n-hexadecylamine, n-octadecylamines, n-eicosylamine, n-docosylamine, n-hexadecenylamines, and n-octadecenylamine. The stated amines may be used individually as co-collectors, although normally amine mixtures with alkyl and/or alkenyl radicals from the fatty acid component of animal or vegetable fats and oils are used.

Suitable alkyl-substituted alkylenediamines for their use as co-collectors conform to the formula (IV), (IV)

in which
$R^6$ and $R^7$ are linear or branched alkyl or alkenyl radicals, and in which
n is 2 to 4.

The preparation of these compounds and their use in flotation are described in DD 64275.

Suitable hydroxyalkyl-substituted alkylenediamines for use as co-collectors conform to the formula (V), in which
$R^8$ and $R^9$ are hydrogen and/or linear alkyl radicals having 1 to 18 carbon atoms, the sum of the carbon atoms of $R^8+R^9$ is 9 to 18, and
n is 2 to 4.

The preparation of compounds of the formula (V) and their use in flotation are described in DE-B 2547987.

The amine compounds mentioned above may be used as such or in the form of their water-soluble salts. The salts are achieved in certain cases by neutralization with equimolar, excess or deficit amounts of acid. Suitable acids are sulfuric acid, phosphoric acid, acetic acid, and formic acid, for example.

Suitable quaternary ammonium compounds for use as co-collectors conform to the formula (VI), in which
$R^{10}$ is a linear alkyl radical having 1 to 18 carbon atoms,
$R^{11}$ is an alkyl radical having 1 to 18 carbon atoms or is a benzyl radical, and
$R^{12}$ and $R^{13}$ may be identical or different and are each an alkyl radical having 1 to 2 carbon atoms, and
X is a halide anion, more particularly a chloride ion.

Preferred quaternary ammonium compounds are those in which $R^{10}$ is an alkyl radical having 8 to 18 carbon atoms and $R^{11}$, $R^{12}$, and $R^{13}$ are identical and are either methyl or ethyl groups, and X is a chloride ion.

The especially preferred cationic co-collectors comprise quaternized N,N-dialkylaminoalkylamides, which conform preferably to the formula (VII), in which
$R^{14}$—CO is an aliphatic, linear or branched acyl radical having 6 to 22 carbon atoms, preferably having 12 to 18 carbon atoms, and containing 0, 1, 2, or 3 double bonds,
[A] is a linear or branched alkylene radical having 1 to 4, preferably 2 or 3, carbon atoms,
$R^{15}$, $R^{16}$, and $R^{17}$ may be identical or different and are each a methyl or ethyl radical, and
X is a halide or an alkylsulfate, especially methosulfate anion.

Preference is given to coconut fatty acid N,N-dimethylaminopropylamide. These products may be prepared, likewise in a known way, for example, by transamidation of N,N-dimethylaminopropane with hydrogenated cocoglycerides and subsequent quaternization by means of dimethyl sulfate. A mixture of collector and co-collector is preferably prepared by the mixing of the esters and the N,N-dialkylalkylamides and, subsequently, joint quaternization.

In accordance with the invention, the ampholytic surfactants which can be used as co-collectors comprise at least one anionic and one cationic group in the molecule. Preferably the anionic groups are sulfonic acid or carboxyl groups and the cationic groups are amino groups, preferably secondary or tertiary amino groups. Suitable ampholytic surfactants are selected more particularly from
sarcosides,
taurides,
N-substituted aminopropionic acids, and
N-(1,2-dicarboxyethyl)-N-alkylsulfosuccinic esters.

Suitable sarcosides for their use as co-collectors conform to the formula (VIII)

in which
$R^{18}$ is an alkyl radical having 7 to 21 carbon atoms, preferably 11 to 17 carbon atoms.

These sarcosides represent known compounds, which can be obtained by known methods. Their use in flotation is described by H. Schubert in "Aufbereitung fester mineralischer Rohstoffe (Dressing fester mineralischer Rohstoffe)", 2nd edition, Leipzig 1977, pp. 310-311 and the literature references cited therein.

Suitable taurides for the use as co-collectors conform to the formula (IX)

in which
$R^{19}$ is an alkyl radical having 7 to 21 carbon atoms, preferably 11 to 17 carbon atoms.

These taurides represent known compounds, which can be obtained by known methods. The use of taurides in flotation is known, cf. H. Schubert, loc. cit.

Preferred N-substituted aminopropionic acids suitable for use as co-collectors conform to the formula (X)

in which
n is 0 or a number from 1 to 4, and
$R^{20}$ is an alkyl or acyl radical having 8 to 22 carbon atoms.

The stated N-substituted aminopropionic acids are likewise known compounds, which are obtainable by known methods. Their use as collectors in flotation is described by H. Schubert, loc. cit., and in Int. J. Min. Proc. 9 (1982), pages 353-384. N-(1,2-Dicarboxyethyl)-N-alkylsulfosuccinic esters suitable in accordance with the invention for use as co-collectors conform to the formula (XI)

in which

R²¹ is an alkyl radical having 8 to 22 carbon atoms, preferably 12 to 18 carbon atoms, and M is a hydrogen ion, an alkali metal cation, or an ammonium ion, preferably a sodium ion.

The aforementioned N-(1,2-dicarboxyethyl)-N-alkylsulfosuccinic esters are known compounds, which may be obtained by known methods. The use of these compounds as collectors in flotation is likewise known; cf. H. Schubert, loc. cit.

The esterquats of the invention and the co-collectors are preferably used in a weight ratio of about 10:90 to about 90:10, preferably about 25:75 to about 75:25, and most preferably about 40:60 to about 60:40.

To achieve economically tenable results in the flotation of non-sulfidic minerals or ores, the collectors or the mixtures of collectors and co-collectors must be used in a certain minimum amount. However, there is also a maximum amount of collector/co-collector that ought not to be exceeded, since otherwise there is excessively vigorous foaming and the selectivity in terms of the valuable minerals goes down.

The amounts with which the collectors are used in accordance with the invention are governed by the nature of the minerals or ores, and are dependent on the initial content of the valuable minerals. Accordingly, the particular amount may vary within wide limits. Generally speaking, the collectors and collector/co-collector mixtures according to the invention are used in amounts of 50 to 2000 g/ton and preferably in amounts of 100 to 1500 g/ton of crude ore.

Typical steps in the flotation process are generally first the dry or preferably wet grinding of the minerals or ores, the suspension of the resultant ground mineral or ore in water in the presence of the flotation reagents, and, preferably after a time of contact with the flotation reagents, the injection of air into the system. The nature of both the starting materials and the flotation assistants are illustrated in more detail below.

Minerals and ores amenable to flotation can be subdivided into the two groups of the polar and nonpolar materials. Since the nonpolar minerals and ores are difficult to hydrate, these materials are classed as hydrophobic. Examples of nonpolar minerals are graphite, molybdenite, diamond, coal, and talc, which are already floatable in their naturally occurring state. In contrast to this, polar minerals and ores have a strong covalent or ionic surface bonding, which by rapid hydrogenation is accessible by water molecules in the form of multilayers. These starting materials are, for example, calcite, malachite, azurite, chrysocolla, wulfenite, cerussite, witherite, magnesite, dolomite, smithsonite, rhodochrosite, siderite, magnetite, monazite, hematite, goethite, chromite, pyrolusite, borax, wolframite, columbite, tantalite, rutile, zircon, hemimorphite, beryl, mica, biotite, quartz, feldspar, kyanite, and garnet. The flotation of non-sulfidic, yet polar minerals and ores is a preferred objective of the present invention.

The flotation behavior of the individual mineral constituents can be controlled to a certain degree through the particle size distribution of the ground mineral. Conversely, however, the particle size may also influence the choice of the collector or collector/co-collector mixture. Generally speaking, though, it may be stated that the particles with increasing particle size must also be hydrophobized to a greater extent before the particles float, this being brought about by means of a higher metering rate. As a general rule, the ores must be ground to an extent such that the individual fine particles consist only of one kind of mineral, namely either of the valuable minerals or of the impurities. The ideal particle size must normally be determined as a function of the specific mineral. In the present case, a particle size distribution of about 5 to 500 μm has proven useful, though in certain cases it may be more practicable to choose a narrower particle size distribution.

For example, silicate-rich ores can be floated outstandingly by flotation using the flotation collectors of the present invention if less than 40% by weight (percent by weight), preferably 30% by weight, more preferably less than 15% by weight of the ore or mineral to be floated is less than 250 μm. In order to be able to carry out optimum flotation, it has emerged that the fraction greater than 125 μm is to be less than 15%, preferably less than 10%, and most preferably less than 5% by weight of the mineral or ore. The lower limit on the particle size is determined not only by the possibility of mechanical size reduction but also by the properties of the mineral constituents on flotation. In general the fraction of particles having a diameter of less than 50 μm ought to be 30% or even 40% by weight. In accordance with the present invention, however, it is particularly advantageous if more than 40% by weight of the particles are smaller than 45 μm.

Additional reagents which alter the surface tension or surface chemistry of the minerals or ore may be used for the flotation. Employed as and when necessary, besides collectors and co-collectors, which have already been mentioned above, are frothers, pH regulators, activators, and depressants.

In particular cases, however, it may be necessary or at least advantageous, depending on the flotation method used, to employ a frother. The addition of a frother is necessary when the foaming property of the collectors or collector/co-collector mixture is not sufficient to produce an appropriately high foam layer which, during the flotation procedure, remains stable enough to collect the mineral particles. Suitable frothers are aliphatic alcohols, natural oils, glycols and glycol ethers.

In particular cases, however, it may be necessary or at least advantageous, depending on the particular flotation method used, to employ a depressant. The addition of a depressant is necessary when the flotation of certain minerals must be suppressed in order to achieve the corresponding yield and the content. Examples of depressants used are natural polysaccharides such as guar, starch, and cellulose. Quebracho, tannin, dextrin, and other chemical derivatives may also be used, especially the derivatives of starch, guar, and cellulose molecules, whose hydroxyl groups may be equipped with a broad range of anionic, cationic, and nonionic functions.

In order to set the rheological behavior of the collectors, it is useful on flotation in accordance with the present invention to add solvent in an amount of 5% to 50% by weight, preferably in an amount of 5% to 40% by weight, and most preferably in an amount of 5% to 30% by weight. Suitable solvents are, for example, aliphatic alcohols having short chain lengths. Hence the flotation assistants in accordance with the present invention may comprise small amounts of glycols, examples being ethylene glycol, propylene glycol or butylene glycol, and also monohydric linear or branched alcohols, examples being ethanol, n-propanol, or isopropanol.

A further object of the present invention is the use of esterquats as collectors for the froth flotation of non-sulfidic minerals or ores. In accordance with the invention the collectors are used in the flotation of non-sulfidic minerals or ores which include, among others, quartz, kaolin, mica, phlogopite, feldspar, silicates and iron oxides.

EXAMPLES

Preparation Example 1

528 g (1.9 mol) of partly hydrogenated palm oil fatty acid, 212 g (1.1 mol) of citric acid, and 0.3 g of hypophosphoric acid were introduced into a reactor with stirring and were heated to 120° C. under reduced pressure of 20 mbar. Then 447 g (3 mol) of triethanolamine were added in portions, with the temperature rising to 130° C. After the end of the addition, the batch was heated to 160° C., the pressure was lowered to 3 mbar, and the mixture was stirred under these conditions over a period of at least 10 h, until the acid number had dropped to a value below 5 mg KOH/g and a typical consistency was obtained. The mixture was subsequently cooled to 60° C., the vacuum was broken by introduction of nitrogen, and 0.6 g of hydrogen peroxide was added in the form of a 30% by weight aqueous solution. For the quaternization, the resulting ester was dissolved in 376 g of isopropyl alcohol and admixed over a period of 1 h with 357 g (2.83 mol) of dimethyl sulfate (DMS) at a rate such that the temperature did not rise above 65° C. After the end of the addition, the batch was left with stirring for a further 2.5 h, with regular sampling to verify the residual DMS content and total nitrogen content. The reaction was ended when a constant total nitrogen content was achieved and no DMS was detected. This gave a product having a solids content of 80% by weight.

Preparation Example 2

902 g (3.2 mol) of oleic acid, 113 g (0.65 mol) of aconitic acid, and 0.9 g of hypophosphorous acid were introduced into a reactor with stirring and were heated to 100° C. under a reduced pressure of 20 mbar. Then 447 g (3 mol) of triethanolamine were added in portions, with the temperature rising to 120° C. After the end of the addition, the batch was heated to 200° C., the pressure was lowered to 3 mbar, and the mixture was stirred under these conditions over a period of at least 6 h, until the acid number had dropped to a value below 5 mg KOH/g and a typical consistency was obtained. The mixture was subsequently cooled to 60° C., the vacuum was broken by introduction of nitrogen, and 0.6 g of hydrogen peroxide was added in the form of a 30% by weight aqueous solution. For the quaternization, the resulting ester was dissolved in 736 g of isopropyl alcohol and admixed over a period of 1 h with 357 g (2.83 mol) of dimethyl sulfate at a rate such that the temperature did not rise above 65° C. After the end of the addition, the batch was left with stirring for a further 2.5 h, with regular sampling to verify the residual DMS content and total nitrogen content. The reaction was ended when a constant total nitrogen content was achieved and no DMS was detected. This gave a product having a solids content of 70% by weight.

Preparation Example 3

590 g (2.1 mol) of distilled mixed fatty acid (primarily $C_{16}$-$C_{20}$), 230 g (1.2 mol) of citric acid, were introduced into a reactor with stirring and were heated to max. 120° C. Then 447 g (3 mol) of triethanolamine were added in portions, with the temperature rising to max. 130° C. After the end of the addition, the batch was heated to 180° C. and the mixture was stirred under these conditions over a period of at least 10 h, until the acid number had dropped to a value below 5 mg KOH/g and a typical consistency was obtained. For the quaternization, the resulting ester was dissolved in 610 g of isopropyl alcohol and admixed over a period of 1 h with 357 g (2.83 mol) of dimethyl sulfate at a rate such that the temperature did not rise above 65° C. After the end of the addition, the batch was left with stirring for a further 2.5 h, with regular sampling to verify the residual DMS content and total nitrogen content. The reaction was ended when a constant total nitrogen content was achieved and no DMS was detected. This gave a product having a solids content of 70% by weight.

Preparation Example 4

28 g (0.2 mol) of caprylic acid, 23 g (0.12 mol) of citric acid, were introduced into a reactor with stirring and were heated to max. 120° C. Then 192 g (0.45 mol) of Genamin C050 (a $C_{12}$/$C_{14}$ amine with 5 mol of ethylene oxide) were added in portions, with the temperature rising to max. 130° C. After the end of the addition, the batch was heated to 180° C. and the mixture was stirred under these conditions over a period of at least 10 h, until the acid number had dropped to a value below 5 mg KOH/g and a typical consistency was obtained. For the quaternization, the resulting ester was dissolved in 286 g of isopropyl alcohol and admixed over a period of 1 h with 53.7 g (0.43 mol) of dimethyl sulfate (DMS) at a rate such that the temperature did not rise above 65° C. After the end of the addition, the batch was left with stirring for a further 2.5 h, with regular sampling to verify the residual DMS content and total nitrogen content. The reaction was ended when a constant total nitrogen content was achieved and no DMS was detected. This gave a product having a solids content of 50% by weight.

Comparative Example [WO2008089906]

In a stirred reactor, 567 g (2.1 mol) of partly hydrogenated palm fatty acid, 219 g (1.5 mol) of adipic acid, and 0.3 g of hypophoric acid hypophosphoric acid were introduced into a reactor with stirring and were heated to 70° C. under reduced pressure of 20 mbar. Then 447 g (3 mol) of triethanolamine were added in portions, with the temperature rising to max. 120° C. After the end of the addition, the batch was heated to 160° C., the pressure was lowered to 3 mbar, and the mixture was stirred under these conditions over a period of 2.5 h, until the acid number had dropped to a value below 5 mg KOH/g. The mixture was subsequently cooled to 60° C., the vacuum was broken by introduction of nitrogen, and 0.6 g of hydrogen peroxide was added in the form of a 30% by weight aqueous solution. For the quaternization, the resulting ester was dissolved in 376 g of isopropyl alcohol and admixed over a period of 1 h with 357 g (2.83 mol) of dimethyl sulfate (DMS) at a rate such that the temperature did not rise above 65° C. After the end of the addition, the batch was left with stirring for a further 2.5 h, with regular sampling to verify the residual DMS content and total nitrogen content. The reaction was ended when a constant total nitrogen content was achieved and no DMS was detected. This gave a product having a solids content of 80% by weight.

Use Examples

The following examples show the superior activity of the new esterquats of the invention relative to collector components from the prior art from WO-2008/089906, especially in comparison to conventional polymeric esterquats synthesized with monobasic and dibasic acids. The tests were carried out under laboratory conditions and, accordingly, the parameters chosen may differ from practice. The reported amounts of the reagents are based on the active substance.

The flotation under laboratory conditions was carried out in accordance with the prior art. The acid-insoluble minerals, which are silicates, are separated from calcite by reverse flotation, by feeding the ground starting material to a flotation cell. In the flotation cell, the starting material is suspended in water. After the addition of a silicate collector and the elapse of a conditioning time, flotation begins. The silicates collect in the froth phase; the calcite remains in the flotation cell.

The following examples illustrate the activity of the collectors of the present invention in comparison to conventional polymeric esterquats synthesized with monobasic and dibasic acids, in the flotation of silicate-containing calcite minerals. The results are shown in Table 1.

Particle size distribution: 60% by weight of all particles>45 μm
Acid-insolubles 2.8% to 3.5% by weight
Calcite: around 96.5-97.2% by weight

TABLE 1

Test results in calcite flotation

| Test results | Metering g/t (Active content) | Mass of tailings [g] | Mass of concentrate [g] | HCl-insolubles content of concentrate [%] | Calcite loss [%] |
|---|---|---|---|---|---|
| Comparative example | 510 | 268.8 | 1447.2 | 0.01 | 13.9 |
|  | 425 | 204.3 | 1511.7 | 0.03 | 10.1 |
|  | 310 | 128.7 | 1587.3 | 0.07 | 5.6 |
| Preparation example 1 | 510 | 106.1 | 1609.9 | 0.01 | 8.7 |
|  | 425 | 73.2 | 1642.8 | 0.05 | 2.4 |
|  | 310 | 58.8 | 1657.3 | 0.13 | 1.6 |
| Preparation example 2 | 425 | 178.5 | 1537.5 | 0.01 | 8.6 |
|  | 320 | 110.9 | 1605.1 | 0.04 | 4.6 |
| Preparation example 3 | 370 | 189.0 | 1527.0 | 0.01 | 9.2 |
|  | 280 | 133.9 | 1582.1 | 0.01 | 5.9 |
|  | 210 | 68.5 | 1647.6 | 0.05 | 2.5 |
| Preparation example 4 | 645 | 136.3 | 1579.7 | 0.02 | 6.1 |
|  | 510 | 106.1 | 1609.9 | 0.02 | 4.3 |
|  | 325 | 65.4 | 1650.6 | 0.09 | 1.9 |

The calcite loss represents the amount of calcite discharged in the reverse flotation together with silicates, iron oxides, and other impurities. The HCl-insolubles content of the concentrate represents the residual amount, still present in the purified calcite, of impurities comprising silicates, iron oxides, etc. The objective is to minimize both the calcite loss and the HCl-insolubles in the concentrate.

Figure 1:
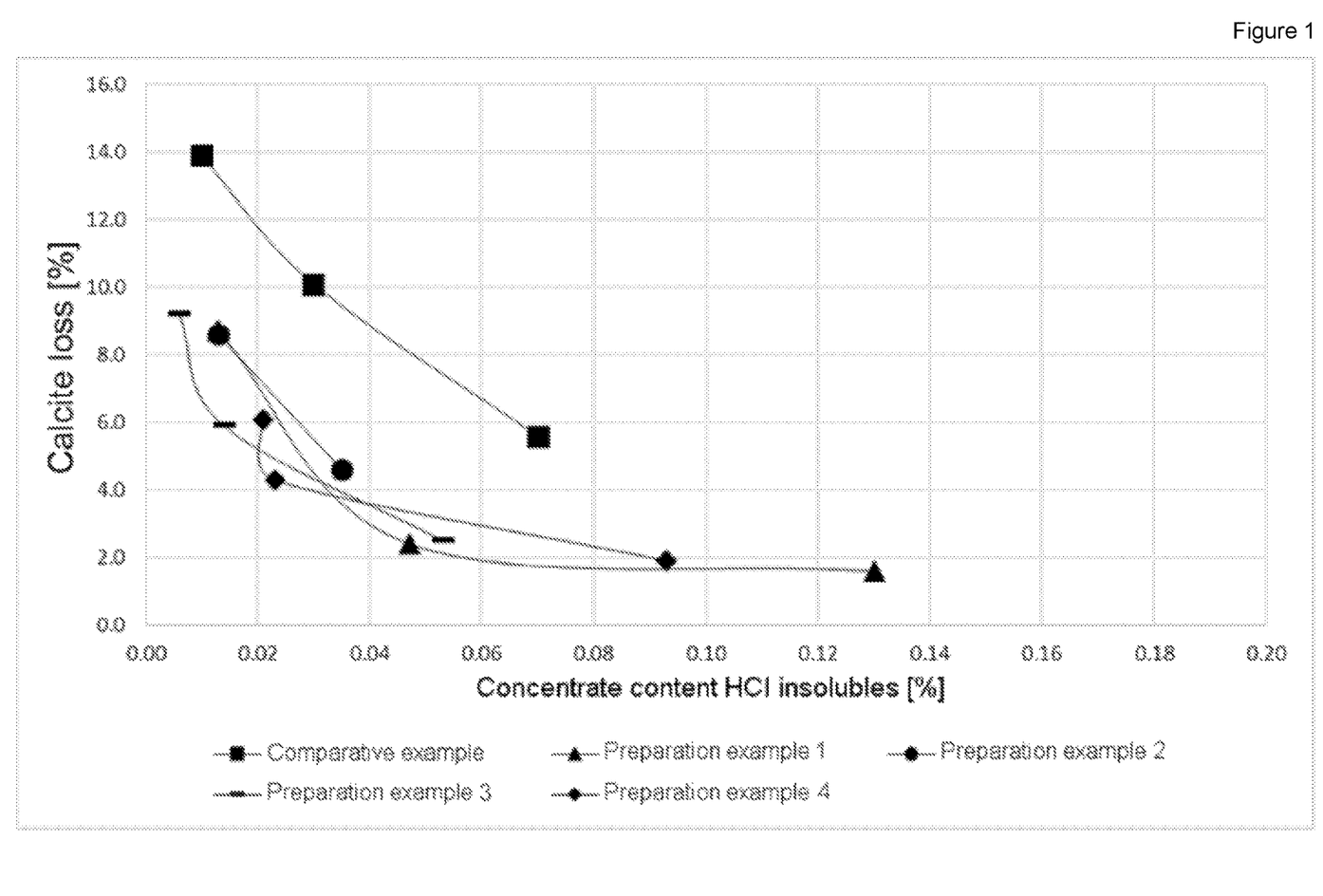
FIG. 1 is substantially a plot of the Concentrate Content HCI Insolubles versus the Calcite Loss for the Comparative Example and the Preparation Examples.

The products of preparation examples 1-4 permit improved reverse calcite flotation by comparison with the comparative example. This is also depicted in graph form in FIG. 1.

The invention claimed is:

1. An esterquat prepared by reacting a di- or trialkanolamine with a mixture of a fatty acid and a polycarboxylic acid and quaternizing the resultant ester subsequently with an alkylating agent, where the di- or trialkanolamine conforms to the formula (I)

in which
R$^1$ and R$^2$ independently of one another are hydroxyalkyl radicals having 1 to 20 carbon atoms, hydroxyalkenyl radicals having 2 to 20 carbon atoms and 1, 2, or 3 double bonds, or adducts of 1 to 20 mol of ethylene oxide onto a hydroxyethyl radical, and
R$^3$ is hydrogen, an alkyl radical having 1 to 20 carbon atoms, an alkenyl radical having 2 to 20 carbon atoms and 1, 2, or 3 double bonds, a hydroxyalkyl radical having 1 to 20 carbon atoms, a hydroxyalkenyl radical having 2 to 20 carbon atoms and 1, 2, or 3 double bonds, or adducts of 1 to 20 mol of ethylene oxide onto a hydroxyethyl radical, and where
the fatty acid conforms to the formula (II), in which
R$^4$ is an aliphatic, linear or branched hydrocarbon radical having 5 to 29 carbon atoms and 0, 1, 2, or 3 double bonds, and where
the polycarboxylic acid conforms to the formula (III)

in which
Y is a carbon atom or a saturated or unsaturated, aliphatic hydrocarbon group having 2 to 5 carbon atoms and optionally carrying one or more hydroxyl groups, and
X is hydrogen, a hydroxyl or a carboxylic acid group.

2. The esterquat as claimed in claim 1, wherein the di- or trialkanolamine of the formula (I) comprises as radicals R$^1$ and R$^2$, independently of one another, hydroxyalkyl radicals having 2 to 5 carbon atoms or hydroxyalkenyl radicals having 2 to 5 carbon atoms and 1, 2, or 3 double bonds, or adducts of 2 to 5 mol of ethylene oxide onto a hydroxyethyl radical.

3. The esterquat as claimed in claim 1, wherein $R^3$ represents alkyl radicals having 1 to 20 carbon atoms, alkenyl radicals having 2 to 20 carbon atoms, hydroxyalkyl radicals having 2 to 5 carbon atoms, or hydroxyalkenyl radicals having 2 to 5 carbon atoms and 1, 2, or 3 double bonds.

4. The esterquat as claimed in claim 1, wherein the di- or trialkanolamine of the formula (I) is selected from the group consisting of methyldiethanolamine (MDA), diethanolamine (DEA), diethoxylated oleylamines, triethanolamine (TEA), and mixtures thereof.

5. The esterquat as claimed in claim 1, wherein in the fatty acid of the formula (II), $R^4$ is an aliphatic, linear or branched radical having 7 to 21 carbon atoms and 0, 1, 2, or 3 double bonds.

6. The esterquat as claimed in claim 1, wherein the fatty acid of the formula (II) are selected from the group consisting of caprylic acid, capric acid, lauric acid, undecylenic acid, isotridecanoic acid, myristic acid, myristoleic acid, palmitic acid, palmitoleic acid, stearic acid, isostearic acid, oleic acid, petroselinic acid, elaidic acid, petroselinic acid, linoleic acid, linolenic acid, eleostearic acid, arachidic acid, gadoleic acid, behenic acid, erucic acid, cetoleic acid, and technical mixtures thereof.

7. The esterquat as claimed in claim 1, wherein the polycarboxylic acid of the formula (III) comprises as radical Y, a saturated or unsaturated aliphatic hydrocarbon group having 3 or 4 carbon atoms, and optionally carrying one or more hydroxyl groups.

8. The esterquat as claimed in claim 1, wherein the polycarboxylic acid is selected from the group consisting of propane-1,2,3-tricarboxylic acid, aconitic acid, isocitric acid citric acid, and mixtures thereof.

9. The esterquat as claimed in claim 1, wherein the fatty acid and the polycarboxylic acid are used in a molar ratio of 1:10 to 10:1.

10. The esterquat as claimed in claim 1, wherein the di- or trialkanolamine and the total amount of the fatty acid and polycarboxylic acid are used in a molar ratio of 1:0.25 to 1:3.0.

11. The esterquat as claimed in claim 1, wherein the alkylating agent is selected from the group consisting of alkyl halides, dialkyl sulfates, dialkyl carbonates, and mixtures thereof.

12. The esterquat as claimed in claim 11, wherein alkyl is methyl or ethyl.

13. A collector for the froth flotation of non-sulfidic minerals and ores comprising at least one esterquat as claimed in claim 1.

14. The collector as claimed in claim 13, wherein the ore is a calcite mineral.

15. A method for flotation of non-sulfidic minerals or ores, wherein the minerals or ores are mixed with water and an esterquat, wherein the esterquat is prepared by reacting a di- or trialkanolamine with a mixture of a fatty acid and a polycarboxylic acid and quaternizing the resultant ester subsequently with an alkylating agent, where the di- or trialkanolamine conforms to the formula (I)

(I)

in which
$R^1$ and $R^2$ independently of one another are hydroxyalkyl radicals having 1 to 20 carbon atoms, hydroxyalkenyl radicals having 2 to 20 carbon atoms and 1, 2, or 3 double bonds, or adducts of 1 to 20 mol of ethylene oxide onto a hydroxyethyl radical, and

$R^3$ is hydrogen, an alkyl radical having 1 to 20 carbon atoms, an alkenyl radical having 2 to 20 carbon atoms and 1, 2, or 3 double bonds, a hydroxyalkyl radical having 1 to 20 carbon atoms, a hydroxyalkenyl radical having 2 to 20 carbon atoms and 1, 2, or 3 double bonds, or adducts of 1 to 20 mol of ethylene oxide onto a hydroxyethyl radical, and where the fatty acid conforms to the formula (II), $$R^4\text{—COOH} \quad \text{(II)}$$

in which
$R^4$ is an aliphatic, linear or branched hydrocarbon radical having 5 to 29 carbon atoms and 0, 1, 2, or 3 double bonds, and where the polycarboxylic acid conforms to the formula (III)

(III)

in which
Y is a carbon atom or a saturated or unsaturated, aliphatic hydrocarbon group having 2 to 5 carbon atoms and optionally carrying one or more hydroxyl groups, and X is hydrogen, a hydroxyl or a carboxylic acid group, to form a suspension, air is introduced into the suspension, to form a floated froth, and the floated froth is subsequently removed.

16. The method as claimed in claim 15, wherein a quaternized N,N-dialkylaminoalkylamide of the formula (VII), (VII)

in which
$R^{14}$—CO is an aliphatic, linear or branched acyl radical having 6 to 22 carbon atoms and containing 0, 1, 2, or 3 double bonds,

[A] is a linear or branched alkylene radical having 1 to 4 carbon atoms, $R^{15}$, $R^{16}$, and $R^{17}$ may be identical or different and each denote a methyl or ethyl radical, and X is a halide or an alkylsulfate anion,
is added as a co-collector.

17. The method as claimed in claim 16, wherein the esterquat and the co-collector of formula (VII) are used in a weight ratio of 10:90 to 90:10.

18. The method as claimed in claim 15, wherein the ore is a calcite mineral.

* * * * *